(12) United States Patent
Jor

(10) Patent No.: US 11,771,809 B2
(45) Date of Patent: Oct. 3, 2023

(54) METHOD FOR STABILIZING DIALYSATE CONSUMPTION FLOW, CORRESPONDING APPARATUS AND CENTRAL DIALYSATE PREPARATION AND DISTRIBUTION SYSTEM

(71) Applicant: Fresenius Medical Care Deutschland GmbH, Bad Homburg (DE)

(72) Inventor: Kee Jor, Hong Kong (CN)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 332 days.

(21) Appl. No.: 17/255,337

(22) PCT Filed: Jun. 26, 2018

(86) PCT No.: PCT/CN2018/092854
§ 371 (c)(1),
(2) Date: Dec. 22, 2020

(87) PCT Pub. No.: WO2020/000178
PCT Pub. Date: Jan. 2, 2020

(65) Prior Publication Data
US 2021/0268161 A1   Sep. 2, 2021

(51) Int. Cl.
*A61M 1/16* (2006.01)

(52) U.S. Cl.
CPC ........ *A61M 1/1656* (2013.01); *A61M 1/1649* (2014.02); *A61M 1/1694* (2013.01); *A61M 2205/3334* (2013.01)

(58) Field of Classification Search
CPC .............. A61M 1/1649; A61M 1/1656; A61M 1/1657; A61M 1/1694; A61M 2205/3334; A61M 2205/84
See application file for complete search history.

(56) References Cited

U.S. PATENT DOCUMENTS

| 4,728,433 A | 3/1988 | Buck et al. |
| 8,506,885 B2 | 8/2013 | Kotsos et al. |

(Continued)

FOREIGN PATENT DOCUMENTS

| CN | 103813816 | 5/2014 |
| CN | 104906645 | 9/2015 |

(Continued)

OTHER PUBLICATIONS

PCT International Preliminary Report on Patentability in International Appln. No. PCT/CN2018/092854, dated Jan. 7, 2021, 6 pages.

(Continued)

*Primary Examiner* — Dirk R Bass
(74) *Attorney, Agent, or Firm* — Fish & Richardson P.C.

(57) ABSTRACT

A method for stabilizing dialysate consumption flow in a central distribution loop for a plurality of dialysis machines comprises: coordinating each dialysate dispensing cycle of active ones of the dialysis machines; calculating dialysate or concentrates consumption based on amount required in each dialysate dispensing cycle of the active dialysis machines; and preparing the dialysate based on the calculated dialysate or concentrates consumption required by the active dialysis machines. Also a corresponding apparatus and a corresponding central dialysate preparation and distribution system are disclosed, wherein the apparatus at least comprises: a coordinating module configured to coordinate each dialysate dispensing cycle of active ones of the dialysis machines; a calculating module configured to calculate dialysate or concentrates consumption based on amount required in each dialysate dispensing cycle of the active dialysis machines; and a mixing control module, for preparing the dialysate based on the calculated dialysate or concentrates consumption.

20 Claims, 4 Drawing Sheets

(56) References Cited

U.S. PATENT DOCUMENTS

2003/0094406 A1    5/2003   Smith
2010/0018923 A1    1/2010   Rohde et al.
2017/0296731 A1   10/2017   Crawford et al.

FOREIGN PATENT DOCUMENTS

| JP | S58-152567  | 9/1983 |
| JP | S60-103972  | 6/1985 |
| JP | H06-245995  | 9/1994 |
| JP | 2003-260130 | 9/2003 |
| JP | 2014-523303 | 9/2014 |

OTHER PUBLICATIONS

PCT International Search Report and Written Opinion in International Appln. No. PCT/CN2018/092854, dated Mar. 29, 2019, 8 pages.
Office Action in Japanese Appln. No. 2020-572732, dated Jul. 26, 2022, 8 pages (with English translation).
Search Report in Japanese Appln. No. 2020-572732, dated Jul. 6, 2022, 58 pages (with English translation).

METHOD FOR STABILIZING DIALYSATE CONSUMPTION FLOW, CORRESPONDING APPARATUS AND CENTRAL DIALYSATE PREPARATION AND DISTRIBUTION SYSTEM

CROSS-REFERENCE TO RELATED APPLICATIONS

The present application is the national stage entry of International Patent Application No. PCT/CN2018/092854, filed on Jun. 26, 2018.

TECHNICAL FIELD

The disclosure relates to a method for stabilizing dialysate consumption flow in a central distribution loop for a plurality of dialysis machines, an apparatus for stabilizing the dialysate consumption flow and a central dialysate preparation and distribution system implementing the method.

BACKGROUND ART

Hemodialysis is a procedure for removing toxic substances and metabolites normally removed by the kidneys, and for aiding in regulation of fluid and electrolyte balance. Hemodialysis is usually accomplished by a dialysis machine using dialysate.

At present, a central dialysate preparation and distribution system is widely used to prepare and distribute the dialysate to a plurality of dialysis machines, for example about 30-40 dialysis machines.

Some parts of the central dialysate preparation and distribution system are normally installed in an isolated equipment room at a distance from treatment area. Such a system usually prepares the dialysate by mixing different concentrates using a volumetric proportioning mixing method. The volumetric proportioning mixing method needs a flow sensor to monitor dialysate consumption to control concentrate pumps to achieve prescribed mixing ratio and amount. One of the challenges is that dialysate flow in the dialysis treatment is pulsatile and these pulsatile flows will be compounded when a plurality of dialysis machines are in operation. It will take time to analyze flow dynamic in consumption to achieve desirable preparation. A sizable dialysate buffer tank is usually required to stabilize conductivity of the dialysate. Moreover, the known central dialysate preparation and distribution system often needs complex flow sensor feedback control algorithm and conductively feedback control algorithm with longer delay time.

SUMMARY OF THE DISCLOSURE

In view of the problems existing in the prior art, an object of the disclosure is to provide a method for stabilizing dialysate consumption flow in a central distribution loop for a plurality of dialysis machines, an apparatus for stabilizing the dialysate consumption flow and a central dialysate preparation and distribution system implementing the method.

For achieving this object, in the first aspect, provided is a method for stabilizing dialysate consumption flow in a central distribution loop for a plurality of dialysis machines, wherein said method comprises steps as follows: coordinating each dialysate dispensing cycle of active ones of the dialysis machines; calculating dialysate or concentrates consumption based on amount required in each dialysate dispensing cycle of the active dialysis machines; and preparing the dialysate based on the calculated dialysate or concentrates consumption required by the active dialysis machines.

According to an optional embodiment, the method further comprises: triggering individual dialysate dispensing sequences in the dialysate dispensing cycle of the active dialysis machines in a predetermined order and/or a predetermined time interval.

According to an optional embodiment, the method further comprises: dividing each dialysate dispensing cycle equally by the number of the active dialysis machines which are operated in a same dialysate flow rate, in which the dialysate dispensing sequences of the active dialysis machines are carried out successively in the predetermined time interval.

According to an optional embodiment, the method further comprises: dividing the active dialysis machines into at least two groups based on different dialysate flow rates; in which each group of active dialysis machines is operated in a same dialysate flow rate.

According to an optional embodiment, the method further comprises: coordinating each dialysate dispensing cycle of one group of active dialysis machines independently from other groups of active dialysis machines.

According to an optional embodiment, the individual dialysate dispensing sequences in the dialysate dispensing cycle of each group of active dialysis machines are triggered in a predetermined order and/or a predetermined time interval.

According to an optional embodiment, the method further comprises: adjusting the dialysate dispensing cycle until the current dialysate dispensing cycle is completed when a treatment parameter or the number of the active dialysis machines is changed.

According to an optional embodiment, the method further comprises: recalculating the dialysate or concentrates consumption based on the amount required in the next dialysate dispensing cycle.

According to an optional embodiment, the method further comprises: distributing a certain amount of dialysate via the active dialysis machines to a drain piping in a predetermined interval to refresh the dialysate in the central distribution loop when no dialysate consumption is made beyond a predetermined period; and/or preventing the dialysate from flowing into a dialyzer of an individual dialysis machine once a dialysate preparation error is detected; and/or preventing the dialysate from flowing into respective dialysis machine once a dialysate flow error in the dialysis machine is detected.

In the second aspect, provided is an apparatus for stabilizing dialysate consumption flow in a central distribution loop for a plurality of dialysis machines, said apparatus at least comprising: a coordinating module configured to coordinate each dialysate dispensing cycle of active ones of the dialysis machines; a calculating module configured to calculate dialysate or concentrates consumption based on amount required in each dialysate dispensing cycle of the active dialysis machines; and a mixing control module, for preparing the dialysate based on the calculated dialysate or concentrates consumption.

According to an optional embodiment, the apparatus further comprises: a triggering module configured to trigger individual dialysate dispensing sequences in the dialysate dispensing cycle of the active dialysis machines in a predetermined order and/or a predetermined time interval.

According to an optional embodiment, the apparatus further comprises: a first dividing module configured to divide each dialysate dispensing cycle equally by the number of the active dialysis machines which are operated in a same dialysate flow rate, in which the dialysate dispensing sequences of the active dialysis machines are carried out successively in the predetermined time interval; and/or a second dividing module configured to divide the active dialysis machines into at least two groups based on different dialysate flow rates; in which each group of active dialysis machines is operated in a same dialysate flow rate.

According to an optional embodiment, the coordinating module is further configured to coordinate each dialysate dispensing cycle of one group of active dialysis machines independently from other groups of active dialysis machines; and/or the individual dialysate dispensing sequences in the dialysate dispensing cycle of each group of active dialysis machines are triggered in a predetermined order and/or a predetermined time interval.

According to an optional embodiment, the apparatus further comprises: an adjusting module configured to adjust the dialysate dispensing cycle until the current dialysate dispensing cycle is completed when a treatment parameter or the number of the active dialysis machines is changed.

According to an optional embodiment, the calculating module is further configured to recalculate the dialysate or concentrates consumption based on the amount required in the next dialysate dispensing cycle.

According to an optional embodiment, the apparatus further comprises: a distribution module configured to distribute a certain amount of dialysate in a predetermined interval to refresh the dialysate in the central distribution loop when no dialysate consumption is made beyond a predetermined period; and/or a preventing module, configured for preventing the dialysate from flowing into a dialyzer of an individual dialysis machine once a dialysate preparation error is detected; and/or for preventing the dialysate from flowing into a respective dialysis machine once a dialysate flow error in the dialysis machine is detected.

In the third aspect, provided is a central dialysate preparation and distribution system for implementing the method for stabilizing dialysate consumption flow in a central distribution loop for a plurality of dialysis machines.

According to an optional embodiment, the central dialysate preparation and distribution system comprises: a dialysate preparation unit which comprises one or more mixing chamber(s), a circulation tube and/or a buffer tank; and/or a dialysate distribution unit configured to distribute the prepared dialysate to the dialysis machines through the central distribution loop which fluidly connects the dialysate preparation unit with the dialysis machines.

According to an optional embodiment, the dialysate distribution unit further comprises a flow monitoring device installed in each dialysis machine or arranged between the central distribution loop and each dialysis machine, which is configured to monitor whether the dialysate flows into the active dialysis machine normally during a dialysis treatment.

According to an optional embodiment, the dialysate distribution unit comprises a static mixer and a recirculating pump for actively mixing.

According to the present disclosure, the stable dialysate consumption flow can be achieved, which will allow for simplifying the design of the dialysate preparation unit. Therefore, a compact dialysate preparation unit can be realized so as to be used near dialysis treatment area, which is very advantageous as the shorter distribution loop will minimize hygiene control burden and the simplified and compact design is cost-efficient. Moreover, the stable dialysate consumption flow allows the dialysate preparation unit to always deliver correct dialysate without the need of some conventional feedback algorithms.

BRIEF DESCRIPTION OF THE DRAWINGS

The disclosure and advantages thereof will be further understood by reading the following detailed description of some preferred exemplary embodiments with reference to the drawings in which.

DETAILED DESCRIPTION OF PREFERRED EMBODIMENTS

Some exemplary embodiments of the present disclosure will be described hereinafter in more details with reference to the drawings to better understand the basic concept of the disclosure.

Firstly, an exemplary central dialysate preparation and distribution system will be described with reference to FIG. 1.

Figure 1:
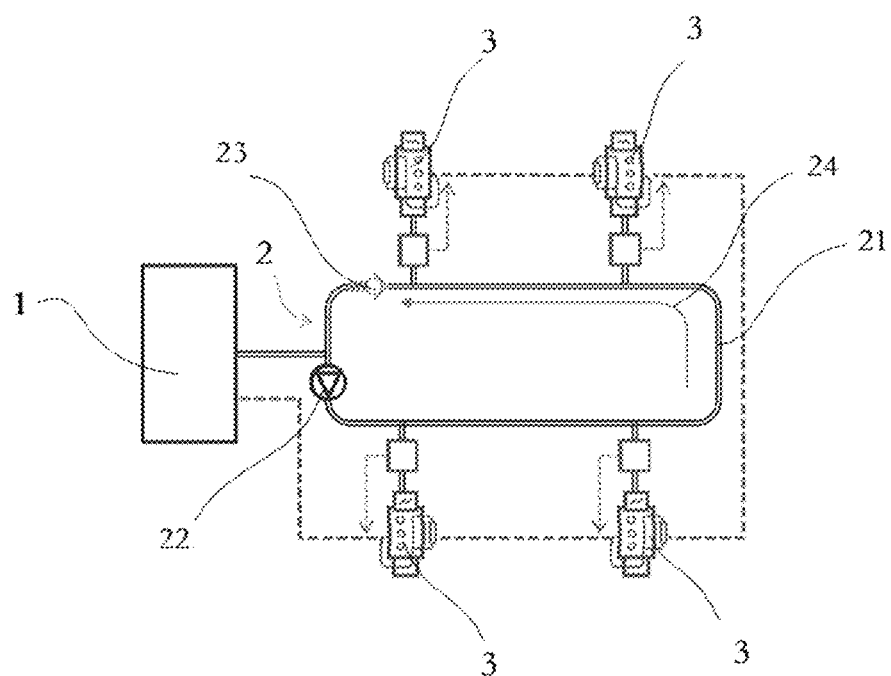
FIG. 1 shows an exemplary central dialysate preparation and distribution system.

As shown in FIG. 1, the central dialysate preparation and distribution system mainly comprises a dialysate preparation unit 1 and a dialysate distribution unit 2 fluidly connected with the dialysate preparation unit 1. The dialysate preparation unit 1 is used for preparing dialysate, for example by using a volumetric proportioning mixing method, and the dialysate distribution unit 2 comprises a central distribution loop 21 fluidly connecting the dialysate preparation unit 1 with a plurality of dialysis machines 3 to distribute the dialysate prepared by the dialysate preparation unit 1 to the dialysis machines 3. The dialysis machines 3 are usually disposed along the central distribution loop 21.

Preferably, a flow pump 22 may be provided at the central distribution loop 21 to produce circulation dialysate flow in the central distribution loop 21, which flow pump is used as a hygiene control measure to avoid stagnant dialysate flow during small or no dialysate consumption period. In addition, such circulation flow improves mixing efficiency in wide ranges of dialysate consumption.

Preferably, the central distribution loop 21 may maintain a holding pressure to load the dialysate into the dialysis machines 3.

Further, a check valve 23 may be provided at the central distribution loop 21 to allow the dialysate to flow in the central distribution loop 21 only in one direction, for example only in a counterclockwise direction 24 in FIG. 1, and/or to set a pressure of the dialysate in the central distribution loop 21. In the dialysis machine 3, a fixed amount of dialysate is usually dispensed in each dialysate dispensing cycle for example by using a control device, such as a balancing chamber device or a duplex pump. Below, the present disclosure will further be described exemplarily only by way of the balancing chamber device as the control device. However, it may be understood by a skilled person in the art that the present disclosure is limited to this.

For example, for the dialysis machine 3 using the balancing chamber device as the control device, the amount of dialysate dispensed in each dialysate dispensing cycle may depend on chamber volume of the balancing chamber device. In production or assembling, even after assembling, the chamber volume of the balancing chamber device may be measured and recorded as one of some key parameters for volumetric proportioning mixing.

Dispensing cycle time of each dialysate dispensing cycle may be calculated from the respective dialysate flow rate and chamber volume.

Preferably, all dialysis machines 3 fluidly connected with the same central distribution loop 21 have the same type of balancing chamber device. Therefore, all dialysis machines 3 may have the same dispensing cycle time if the same dialysate flow rate is set in dialysis treatment.

The dialysate preparation unit 1 may obtain some parameters, including but not limited to the dialysate flow rates and chamber volumes of active ones of the dialysis machines 3, to calculate the total dialysate consumption flow, and then prepare the corresponding amount of dialysate based on the calculated dialysate consumption flow. The preparation process needs to be adjusted accordingly with change of the actual dialysate consumption flow.

Figure 2:
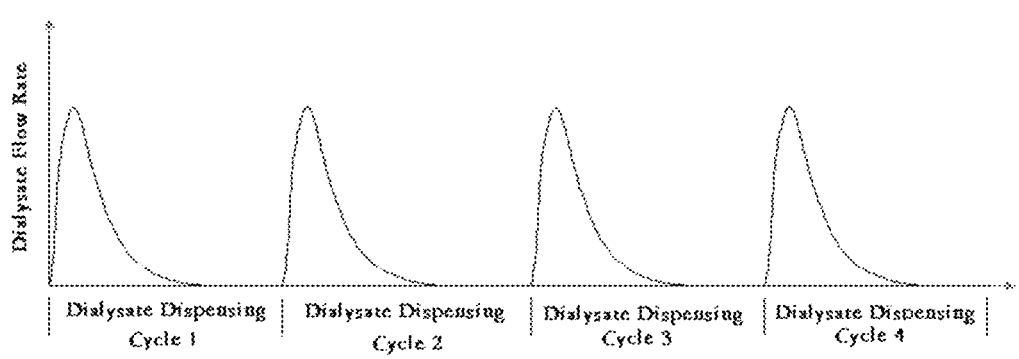
FIG. 2 shows pulsatile dialysate flow rate in four dialysate dispensing cycles of one dialysis machine.

However, in an actual operation, one or more of the dialysis machines 3 may be activated or deactivated irregularly and/or the number of the active dialysis machines 3 may change at any time, which will lead to irregular fluctuation of the dialysate consumption flow such that the dialysate consumption flow in the central distribution loop 21 may become unstable, even if a flow sensor is provided to monitor the dialysate consumption flow as a feedback. Further, since the dialysate flow rate into individual active dialysis machines 3 in each dialysate dispensing cycle is pulsatile and other some parameters also may change, the dialysate consumption flow may become more unstable. Therefore, it is necessary to provide a method for stabilizing the dialysate consumption flow in the central distribution loop 21. FIG. 2 shows the pulsatile dialysate flow rate in four dialysate dispensing cycles of one dialysis machine 3.

According to the present disclosure, each dialysate dispensing cycle of the active dialysis machines 3 is coordinated to smooth the fluctuation of the dialysate consumption flow. In this case, the dialysate or concentrates consumption can be calculated more reliably based on amount required in each dialysate dispensing cycle of the active dialysis machines 3 and then the dialysate is prepared based on the calculated dialysate or concentrates consumption required by the active dialysis machines 3.

According to one exemplary embodiment of the present disclosure, individual dialysate dispensing sequences in the dialysate dispensing cycle of the active dialysis machines 3 may be triggered in a predetermined order and/or a predetermined time interval.

Only for ease of description of such a coordinating concept, these four dialysis machines 3 shown in FIG. 1 are known sequentially as machine #1, machine #2, machine #3 and machine #4 in a counterclockwise direction and are all active. It may be understood by the skilled person in the art that the actual number of the dialysis machines 3 is not limited to this and only some of the dialysis machines 3 may be activated.

Figure 3:
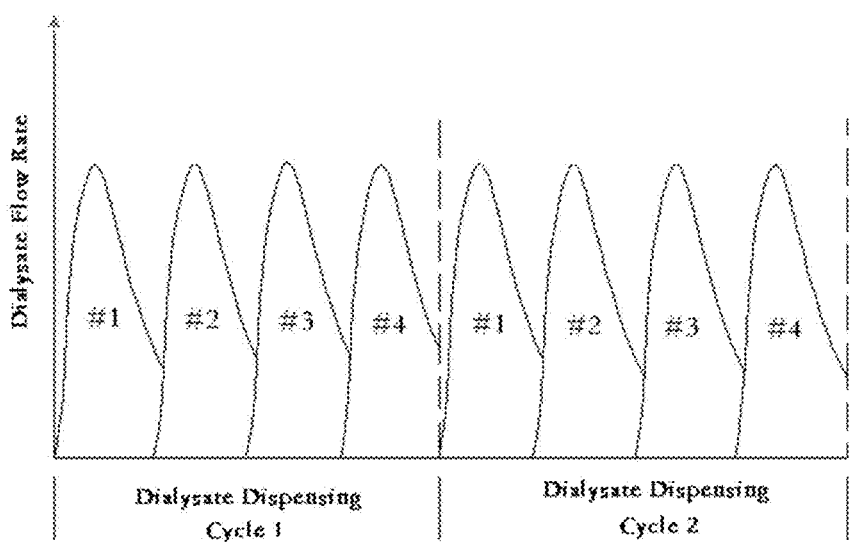
FIG. 3 shows two coordinated dialysate dispensing cycles of active dialysis machines.

FIG. 3 shows two coordinated dialysate dispensing cycles of the active dialysis machines 3.

As shown in FIG. 3, the individual dialysate dispensing sequences in the dialysate dispensing cycle of machine #1, machine #2, machine #3 and machine #4 are triggered in a predetermined order, for example from machine #1 to machine #4, which will make the dialysate consumption flow more stable. If the individual dialysate dispensing sequences in the dialysate dispensing cycle of the four dialysis machines 3 are triggered synchronously, these dialysate dispensing sequences will be superimposed such that the dialysate consumption flow will fluctuate largely as the individual dialysate flow rate is pulsatile.

Of course, if the individual dialysate dispensing sequences in the dialysate dispensing cycle of these dialysis machines 3 are triggered in a predetermined time interval, the dialysate consumption flow also can be stabilized.

If these dialysis machines 3 are operated in a same dialysate flow rate, the fluctuation of the dialysate consumption flow caused by each dialysis machine 3 may be at least similar. In this case, it is advantageous that the dialysate dispensing sequences of the dialysis machines 3 are carried out successively in the predetermined time interval.

According to one exemplary embodiment of the present disclosure, the predetermined time interval may be preferably determined by dividing each dialysate dispensing cycle equally by the number of the active dialysis machines 3.

If the dialysis machines 3 fluidly connected with the same central distribution loop 21 are operated in different dialysate flow rates, the fluctuation of the dialysate consumption flow caused by each dialysis machine 3 may be different. In this case, according to one exemplary embodiment of the present disclosure, the active dialysis machines 3 are divided into at least two groups based on the different dialysate flow rates such that each group of active dialysis machines 3 is operated in a same dialysate flow rate.

According to one exemplary embodiment of the present disclosure, each dialysate dispensing cycle of one group of active dialysis machines 3 may be coordinated independently from other groups of active dialysis machines 3.

Further, each dialysate dispensing cycle of one group of active dialysis machines 3 may be coordinated in a similar way as described with reference to FIG. 3. That is to say, the individual dialysate dispensing sequences in the dialysate dispensing cycle of each group of active dialysis machines 3 may be triggered in a respective predetermined order and/or a respective predetermined time interval.

Figure 4:
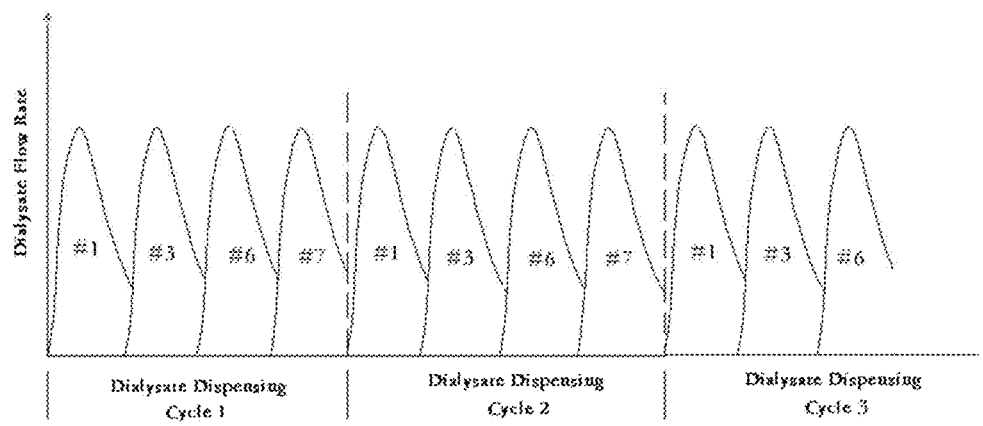
FIG. 4 shows a coordinating method for the active dialysis machines operated in different dialysate flow rates.
Figure 4:
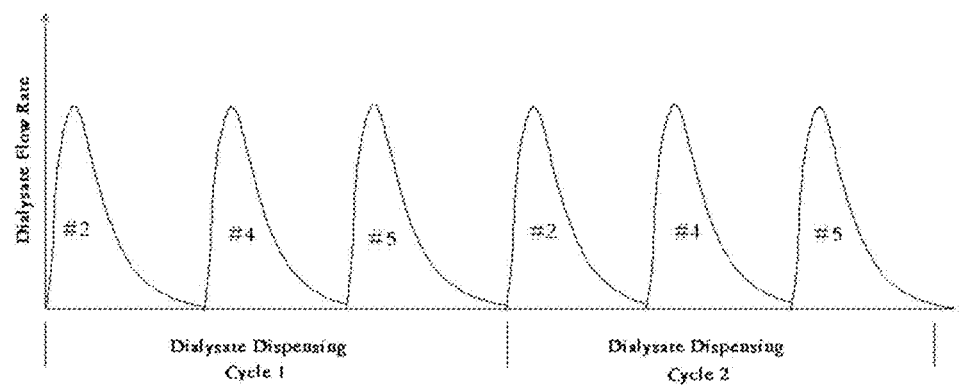

For example, FIG. 4 shows such a coordinating concept for the active dialysis machines 3 operated in different dialysate flow rates. It is assumed that a total of seven active dialysis machines 3 are operated in different dialysate flow rates, in which a first group of machines #1, #3, #6 and #7 is operated in a first same dialysate flow rate, for example 800 ml/min, while a second group of machines #2, #4 and #5 is operated in a second same dialysate flow rate, for example, 500 ml/min, different from the first same dialysate flow rate. As shown in FIG. 4, the first group of machines and the second group of machines are coordinated separately as explained above with reference to FIG. 3.

For the central dialysate preparation and distribution system, one or more other dialysis machines may be activated during the current dialysate dispensing cycle and/or one or more of the active dialysis machines 3 may be deactivated during the current dialysate dispensing cycle such that the number of the active dialysis machines 3 is changed. Further, a treatment parameter, for example the dialysate flow rate of one or more of the active dialysis machines 3, also may change during the current dialysate dispensing cycle. In this case, it is advantageous that the dialysate dispensing cycle may be adjusted until the current dialysate dispensing cycle is completed when a treatment parameter and/or the number of the active dialysis machines 3 is changed.

Of course, the dialysate or concentrates consumption should be recalculated based on the amount required in the next dialysate dispensing cycle of the group of machines with dominating dialysate consumption at the same flow rate.

According to one exemplary embodiment of the present disclosure, a certain amount of dialysate is distributed in a predetermined interval to refresh the dialysate in the central distribution loop 21 when no dialysate consumption is made beyond a predetermined period, which can achieve hygiene control. For example, if the dialysate preparation unit 1 were in operation but no dialysate consumption for a long time, as a hygiene control measure, all active dialysis machines 3 are controlled to dispense a fixed amount of dialysate to drain in regular interval, for example 30 min, to refresh the dialysate in the central distribution loop 21 as well as the dialysis machines 3. Given the shorter central distribution loop 21, one main endotoxin retentive filter (ETRF) in the central distribution loop 21 will be sufficient for high flow treatment.

According to one exemplary embodiment of the present disclosure, the dialysate may be prevented from flowing into a dialyzer of an individual dialysis machine once a dialysate preparation error is detected, which will avoid any possible treatment risks. The dialysate preparation error can trigger audio and/or visual alarm to alert operator.

According to one exemplary embodiment of the present disclosure, the dialysate may be prevented from flowing into a respective dialysis machine once a dialysate flow error in the dialysis machine is detected. For example, the central distribution loop 21 comprises a flow monitoring device installed in each dialysis machine 3 or arranged between the central distribution loop 21 and the respective dialysis machine 3 to monitor whether there is adequate dialysate flow, in particular there is dialysate flow, normally in a dialysis treatment of the active dialysis machine 3. If there is not adequate dialysate flow, in particular no dialysate flow in a dialysis treatment of the dialysis machine 3, the dialysate should be prevented from flowing into the dialysis machine 3. The dialysate flow error may lead to dialysate mixing error of the dialysate preparation unit 1 and thus should trigger audio and/or visual alarm to alert operator.

Figure 5:
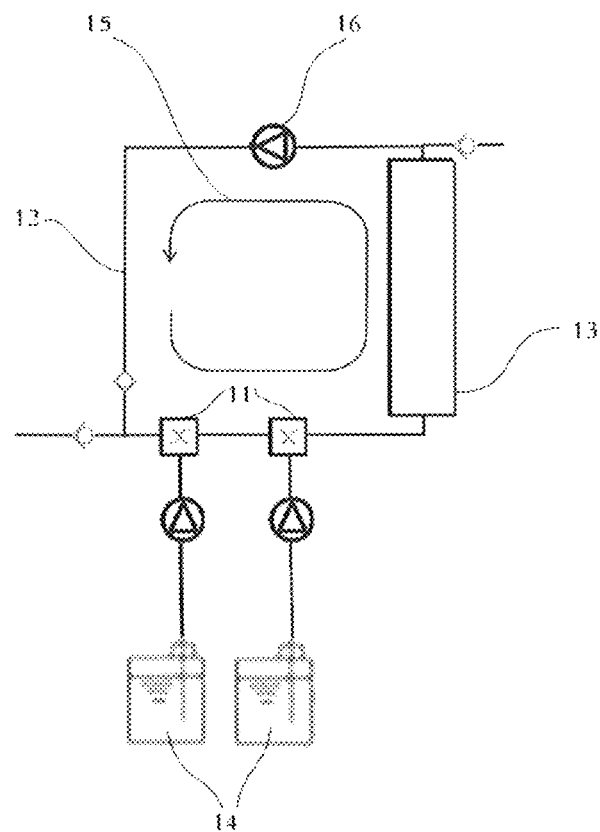
FIG. 5 schematically shows an exemplary embodiment of the dialysate preparation unit.

FIG. 5 schematically shows an exemplary embodiment of the dialysate preparation unit 1. As shown in FIG. 5, the dialysate preparation unit 1 comprises two mixing chambers 11, a circulation tube 12 and a buffer tank 13, wherein the two mixing chambers 11 are configured to receive concentrates from concentrate containers 14 and are fluidly connected with the circulation tube 12 and the buffer tank 13. It may be understood that only one mixing chamber also is possible. In such a dialysate preparation unit 1, high speed recirculation flow 15 is generated in the circulation tube 12 by a recirculating pump 16 arranged in the circulation tube 12. In a certain case, the buffer tank is optional as the stable dialysate consumption flow helps to keep conductivity of the dialysate stable.

Figure 6:
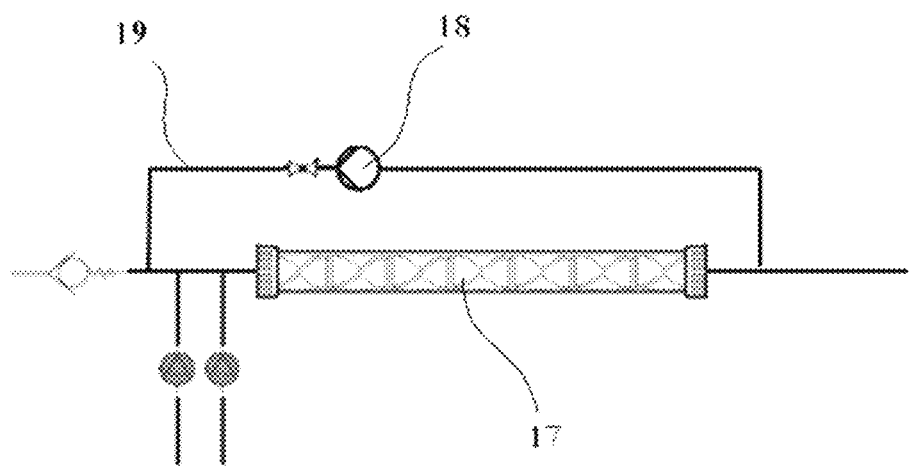
FIG. 6 schematically shows another exemplary embodiment of the dialysate preparation unit.

FIG. 6 schematically shows another exemplary embodiment of the dialysate preparation unit 1. As shown in FIG. 6, the dialysate preparation unit 1 comprises a static mixer 17, preferably a helical static mixer and a recirculating pump 18 for actively mixing, preferably a recirculating gear pump. The static mixer 17 and the recirculating pump 18 are connected fluidly by a circulation tube 19. Such a dialysate preparation unit 1 can not only achieve an effective mixing to deliver wide range of mix-on-demand dialysate flow, but also achieve better hygiene control at a low consumption by using the recirculating pump 18 to keep sufficient fluid flow in the static mixer 17. Further, reliable mixing is made directly in the circulation tube 19 and thus no tank is required, which will reduce size of the dialysate preparation unit 1.

According to one exemplary embodiment of the present disclosure, the dialysate preparation unit 1 is connected communicatively with the dialysis machines 3 by a control link or a system network such that the dialysate preparation unit 1 can obtain some parameters from the dialysis machines 3 and control the dialysis machines 3, for example coordinate each dialysate dispensing cycle of the active dialysis machines 3.

According to one exemplary embodiment of the present disclosure, the dialysis machine 3 is configured to store some parameters, for example a dispensing amount per cycle/actual chamber volume, in a memory thereof. Preferably, the parameters can be transmitted to the dialysate preparing unit 1 when the dialysis machine 3 is activated to receive the dialysate, in particular powered on.

Figure 7:
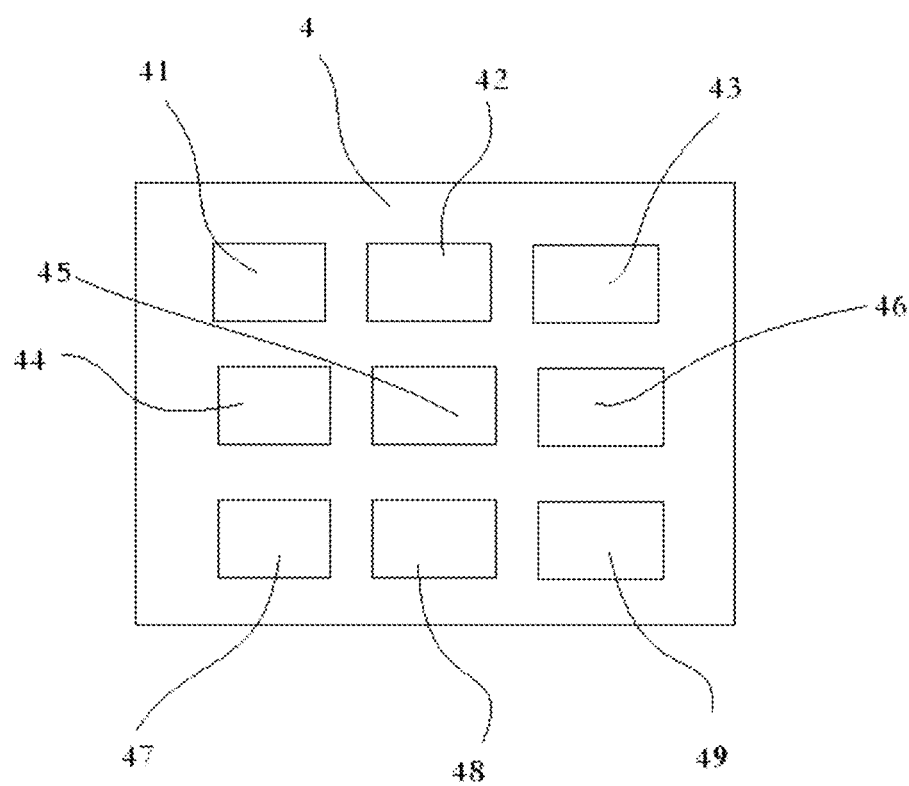
FIG. 7 schematically shows an apparatus for stabilizing dialysate consumption flow in the central distribution loop for the dialysis machines.

FIG. 7 schematically shows an apparatus 4 for stabilizing dialysate consumption flow in the central distribution loop 21 for the dialysis machines 3. The apparatus as a central control module at least comprises: a coordinating module 41 configured to coordinate each dialysate dispensing cycle of active ones of the dialysis machines 3; a calculating module 42 configured to calculate dialysate or concentrates consumption based on amount required in each dialysate dispensing cycle of the active dialysis machines 3; and a mixing control module 43, for preparing the dialysate based on the calculated dialysate or concentrates consumption.

According to one exemplary embodiment of the present disclosure, the apparatus 4 further comprises: a triggering module 44 configured to trigger individual dialysate dispensing sequences in the dialysate dispensing cycle of the active dialysis machines 3 in a predetermined order and/or a predetermined time interval.

According to one exemplary embodiment of the present disclosure, the apparatus 4 further comprises: a first dividing module 45 configured to divide each dialysate dispensing cycle equally by the number of the active dialysis machines 3 which are operated in a same dialysate flow rate, in which the dialysate dispensing sequences of the active dialysis machines 3 are carried out successively in the predetermined time interval; and/or a second dividing module 46 configured to divide the active dialysis machines 3 into at least two groups based on different dialysate flow rates; in which each group of active dialysis machines 3 is operated in a same dialysate flow rate.

According to one exemplary embodiment of the present disclosure, the coordinating module 41 is further configured to coordinate each dialysate dispensing cycle of one group of active dialysis machines 3 independently from other groups of active dialysis machines 3; and/or the individual dialysate dispensing sequences in the dialysate dispensing cycle of each group of active dialysis machines 3 are triggered in a predetermined order and/or a predetermined time interval.

According to one exemplary embodiment of the present disclosure, the apparatus 4 further comprises: an adjusting module 47 configured to adjust the dialysate dispensing cycle until the current dialysate dispensing cycle is completed when a treatment parameter or the number of the active dialysis machines 3 is changed.

According to one exemplary embodiment of the present disclosure, the calculating module 42 is further configured to recalculate the dialysate or concentrates consumption based on the amount required in the next dialysate dispensing cycle.

According to one exemplary embodiment of the present disclosure, the apparatus 4 further comprises: a distribution module 48 configured to distribute a certain amount of dialysate in a predetermined interval to refresh the dialysate in the central distribution loop 21 when no dialysate consumption is made beyond a predetermined period; and/or a preventing module 49, configured for preventing the dialysate from flowing into an individual dialysis machine 3 once a dialysate preparation error is detected, and/or for preventing the dialysate from flowing into a respective dialysis machine 3 once a dialysate flow error in the dialysis machine 3 is detected.

It may be understood by the skilled person in the art that one or more of the above modules 41-49 can be combined in any suitable manner.

According to the present disclosure, a stable dialysate consumption flow can be achieved by coordinating each dialysate dispensing cycle of the active dialysis machines, which will allow for simplifying the design of the dialysate preparation unit, for example reducing size of the buffer tank, even not requiring the buffer tank. Therefore, a compact dialysate preparation unit can be realized so as to be used inside dialysis treatment area, which is very advantageous as the shorter distribution loop will minimize hygiene control burden and the simplified and compact design is cost-efficient. Moreover, the stable dialysate consumption flow allows the dialysate preparation unit to always deliver correct dialysate without the need of some conventional feedback algorithm, such as flow sensor feedback control algorithm and conductivity feedback control algorithm to analyze dialysate consumption change. Simple conductivity measurement in an outlet of the dialysate preparation unit is sufficient as safety measure to monitor dialysate quality.

While certain embodiments have been described, these embodiments have been presented by way of example only, and are not intended to limit the scope of the disclosure. The attached claims and their equivalents are intended to cover all the modifications, substitutions and changes as would fall within the scope and spirit of the disclosure.

The invention claimed is:

1. A method for stabilizing dialysate consumption flow in a central distribution loop (21) for a plurality of dialysis machines (3), wherein said method comprises steps as follows:
   coordinating each dialysate dispensing cycle of active ones of the dialysis machines (3);
   calculating dialysate or concentrates consumption based on amount required in each dialysate dispensing cycle of the active dialysis machines (3); and
   preparing the dialysate based on the calculated dialysate or concentrates consumption required by the active dialysis machines (3).

2. The method according to claim 1, wherein the method further comprises:
   triggering individual dialysate dispensing sequences in the dialysate dispensing cycle of the active dialysis machines (3) in a predetermined order and/or a predetermined time interval.

3. The method according to claim 2, wherein the method further comprises:
   dividing each dialysate dispensing cycle equally by the number of the active dialysis machines (3) which are operated in a same dialysate flow rate, in which the dialysate dispensing sequences of the active dialysis machines (3) are carried out successively in the predetermined time interval.

4. The method according to claim 2, wherein the method further comprises:
   dividing the active dialysis machines (3) into at least two groups based on different dialysate flow rates; in which each group of active dialysis machines (3) is operated in a same dialysate flow rate.

5. The method according to claim 4, wherein the method further comprises:
   coordinating each dialysate dispensing cycle of one group of active dialysis machines (3) independently from other groups of active dialysis machines (3).

6. The method according to claim 5, wherein
   the individual dialysate dispensing sequences in the dialysate dispensing cycle of each group of active dialysis machines (3) are triggered in a predetermined order and/or a predetermined time interval.

7. The method according to claim 1, wherein the method further comprises:
   adjusting the dialysate dispensing cycle until the current dialysate dispensing cycle is completed when a treatment parameter or the number of the active dialysis machines (3) is changed.

8. The method according to claim 7, wherein the method further comprises:
   recalculating the dialysate or concentrates consumption based on the amount required in the next dialysate dispensing cycle.

9. The method according to claim 1, wherein the method further comprises:
   distributing a certain amount of dialysate via the active dialysis machine (3) to a drain piping in a predetermined interval to refresh the dialysate in the central distribution loop (21) when no dialysate consumption is made beyond a predetermined period; and/or
   preventing the dialysate from flowing into a dialyzer of an individual dialysis machine (3) once a dialysate preparation error is detected; and/or
   preventing the dialysate from flowing into respective dialysis machine (3) once a dialysate flow error in the dialysis machine (3) is detected.

10. An apparatus (4) for stabilizing dialysate consumption flow in a central distribution loop (21) for a plurality of dialysis machines (3), said apparatus (4) at least comprising:
    a coordinating module (41) configured to coordinate each dialysate dispensing cycle of active ones of the dialysis machines (3);
    a calculating module (42) configured to calculate dialysate or concentrates consumption based on amount required in each dialysate dispensing cycle of the active dialysis machines (3); and
    a mixing control module (43), for preparing the dialysate based on the calculated dialysate or concentrates consumption.

11. The apparatus (4) according to claim 10, wherein the apparatus (4) further comprises:
    a triggering module (44) configured to trigger individual dialysate dispensing sequences in the dialysate dispensing cycle of the active dialysis machines (3) in a predetermined order and/or a predetermined time interval.

12. The apparatus (4) according to claim 11, wherein the apparatus (4) further comprises:

a first dividing module (45) configured to divide each dialysate dispensing cycle equally by the number of the active dialysis machines (3) which are operated in a same dialysate flow rate, in which the dialysate dispensing sequences of the active dialysis machines (3) are carried out successively in the predetermined time interval; and/or a second dividing module (46) configured to divide the active dialysis machines (3) into at least two groups based on different dialysate flow rates; in which each group of active dialysis machines (3) is operated in a same dialysate flow rate.

13. The apparatus (4) according to claim 12, wherein the coordinating module (41) is further configured to coordinate each dialysate dispensing cycle of one group of active dialysis machines (3) independently from other groups of active dialysis machines (3); and/or the individual dialysate dispensing sequences in the dialysate dispensing cycle of each group of active dialysis machines (3) are triggered in a predetermined order and/or a predetermined time interval.

14. The apparatus (4) according to claim 10, wherein the apparatus further comprises:

an adjusting module (47) configured to adjust the dialysate dispensing cycle until the current dialysate dispensing cycle is completed when a treatment parameter or the number of the active dialysis machines (3) is changed.

15. The apparatus (4) according to claim 14, wherein the calculating module (42) is further configured to recalculate the dialysate or concentrates consumption based on the amount required in the next dialysate dispensing cycle.

16. The apparatus (4) according to claim 10, wherein the apparatus further comprises:

a distribution module (48) configured to distribute a certain amount of dialysate in a predetermined interval to refresh the dialysate in the central distribution loop (21) when no dialysate consumption is made beyond a predetermined period; and/or a preventing module (49), configured for preventing the dialysate from flowing into a dialyzer of an individual dialysis machine once a dialysate preparation error is detected; and/or for preventing the dialysate from flowing into a respective dialysis machine (3) once a dialysate flow error in the dialysis machine (3) is detected.

17. A central dialysate preparation and distribution system for stabilizing dialysate consumption flow in a central distribution loop (21) for a plurality of dialysis machines (3), the system comprising a central control module configured to perform the method according to claim 1.

18. The central dialysate preparation and distribution system according to claim 17, wherein the central dialysate preparation and distribution system comprises:

a dialysate preparation unit (1) which comprises one or more mixing chamber(s) (11), a circulation tube (12) and/or a buffer tank (13); and/or a dialysate distribution unit (2) configured to distribute the prepared dialysate to the dialysis machines (3) through the central distribution loop (21) which fluidly connects the dialysate preparation unit (1) with the dialysis machines (3).

19. The central dialysate preparation and distribution system according to claim 18, wherein the dialysate distribution unit further comprises a flow monitoring device installed in each dialysis machine (3) or arranged between the central distribution loop (21) and each dialysis machine (3), which is configured to monitor whether the dialysate flows into the active dialysis machine (3) normally during a dialysis treatment.

20. The central dialysate preparation and distribution system according to claim 18, wherein the dialysate distribution unit (2) comprises a static mixer (17) and a recirculating pump (18) for actively mixing.

\* \* \* \* \*